(12) United States Patent
Moffitt

(10) Patent No.: US 8,934,979 B2
(45) Date of Patent: Jan. 13, 2015

(54) NEUROSTIMULATION SYSTEM FOR SELECTIVELY ESTIMATING VOLUME OF ACTIVATION AND PROVIDING THERAPY

(75) Inventor: Michael A. Moffitt, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 109 days.

(21) Appl. No.: 13/336,580

(22) Filed: Dec. 23, 2011

(65) Prior Publication Data

US 2012/0165898 A1 Jun. 28, 2012

Related U.S. Application Data

(60) Provisional application No. 61/427,441, filed on Dec. 27, 2010.

(51) Int. Cl.
 A61N 1/00 (2006.01)
 A61N 1/372 (2006.01)
(52) U.S. Cl.
 CPC .................. *A61N 1/37247* (2013.01)
 USPC .................. 607/45; 607/60; 607/46; 607/59
(58) Field of Classification Search
 USPC ......................... 607/30, 45, 46, 59
 See application file for complete search history.

(56) References Cited

U.S. PATENT DOCUMENTS 6,516,227 B1 2/2003 Meadows et al.
6,609,032 B1* 8/2003 Woods et al. .................. 607/46
6,845,267 B2 1/2005 Harrison et al.
6,895,280 B2 5/2005 Meadows et al.
6,950,707 B2 9/2005 Whitehurst
(Continued)

FOREIGN PATENT DOCUMENTS

WO WO 2008/018067 A2 2/2008
WO WO 2008/018067 A3 2/2008
(Continued)

OTHER PUBLICATIONS

U.S. Appl. No. 61/374,879, User Interface for Segmented Neurostimulation Leads, Inventor: Michael A. Moffitt, et al., filed Aug. 18, 2010.
(Continued)

*Primary Examiner* — Michael Kahelin
*Assistant Examiner* — Mallika D Fairchild
(74) *Attorney, Agent, or Firm* — Vista IP Law Group LLP

(57) ABSTRACT

An external control device, neurostimulation system, and method of programming a neurostimulator. A volume of tissue activation for each of a first one or more candidate stimulation parameter sets is simulated without conveying electrical stimulation energy into the tissue. One of the first candidate stimulation parameter set(s) is selected based on each simulated volume of tissue activation. Electrical stimulation energy is conveyed into the tissue in accordance with a second one or more candidate stimulation parameter sets, wherein the initial one of the second candidate stimulation parameter set(s) is the selected one of the first candidate stimulation parameter set(s). One of the second candidate stimulation parameter set(s) is selected based on a therapeutic efficacy of the electrical stimulation energy conveyed into the tissue. The neurostimulator is programmed with the selected one of the second candidate stimulation parameter set(s).

30 Claims, 8 Drawing Sheets

(56) References Cited

U.S. PATENT DOCUMENTS

| | | |
|---|---|---|
| 6,993,384 B2 | 1/2006 | Bradley et al. |
| 7,650,184 B2 | 1/2010 | Walter |
| 8,019,439 B2 | 9/2011 | Kuzma et al. |
| 2007/0168004 A1 | 7/2007 | Walter |
| 2007/0168007 A1 | 7/2007 | Kuzma et al. |
| 2007/0203546 A1 | 8/2007 | Stone et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2010/0010566 A1 | 1/2010 | Thacker et al. |
| 2010/0049276 A1 | 2/2010 | Blum et al. |
| 2010/0121409 A1 | 5/2010 | Kothandaraman et al. |

FOREIGN PATENT DOCUMENTS

| | | |
|---|---|---|
| WO | WO 2009/139917 A2 | 11/2009 |
| WO | WO 2009/139917 A3 | 11/2009 |
| WO | WO 2010/065888 A1 | 6/2010 |
| WO | WO 2010/065888 A2 | 6/2010 |
| WO | WO 2010/065888 A3 | 6/2010 |

OTHER PUBLICATIONS

PCT International Search Report for PCT/US2011/067214, Applicant: Boston Scientific Neuromodulation Corporation, Form PCT/ISA/210 and 220, dated May 8, 2012 (6pages).

PCT Written Opinion of the International Search Authority for PCT/US2011/067214, Applicant: Boston Scientific Neuromodulation Corporation, Form PCT/ISA/237, dated May 8, 2012 (7pages).

Frankemolle A.M., et al., Reversing Cognitive-Motor Impairments in Parkinson's Disease Patients Using a Computational Modelling Approach to Deep Brain Stimulation Programming, Brain Mar. 2010, 133 (Pt 3): 746-761, Epub Jan. 7, 2010.

Hunka K., et al., Nursing Time to Program and Assess Deep Brain Stimulators in Movement Disorder Patients, J. Neursci Nurs., vol. 37, No. 4, pp. 204-210 (Aug. 2005).

PCT International Preliminary Report on Patentability (Chapter I of the Patent Cooperation Treaty) for PCT/US2011/067214, Applicant: Boston Scientific Neuromodulation Corporation, Form PCT/IB/326 and 373, dated Jul. 11, 2013 (9pages).

* cited by examiner

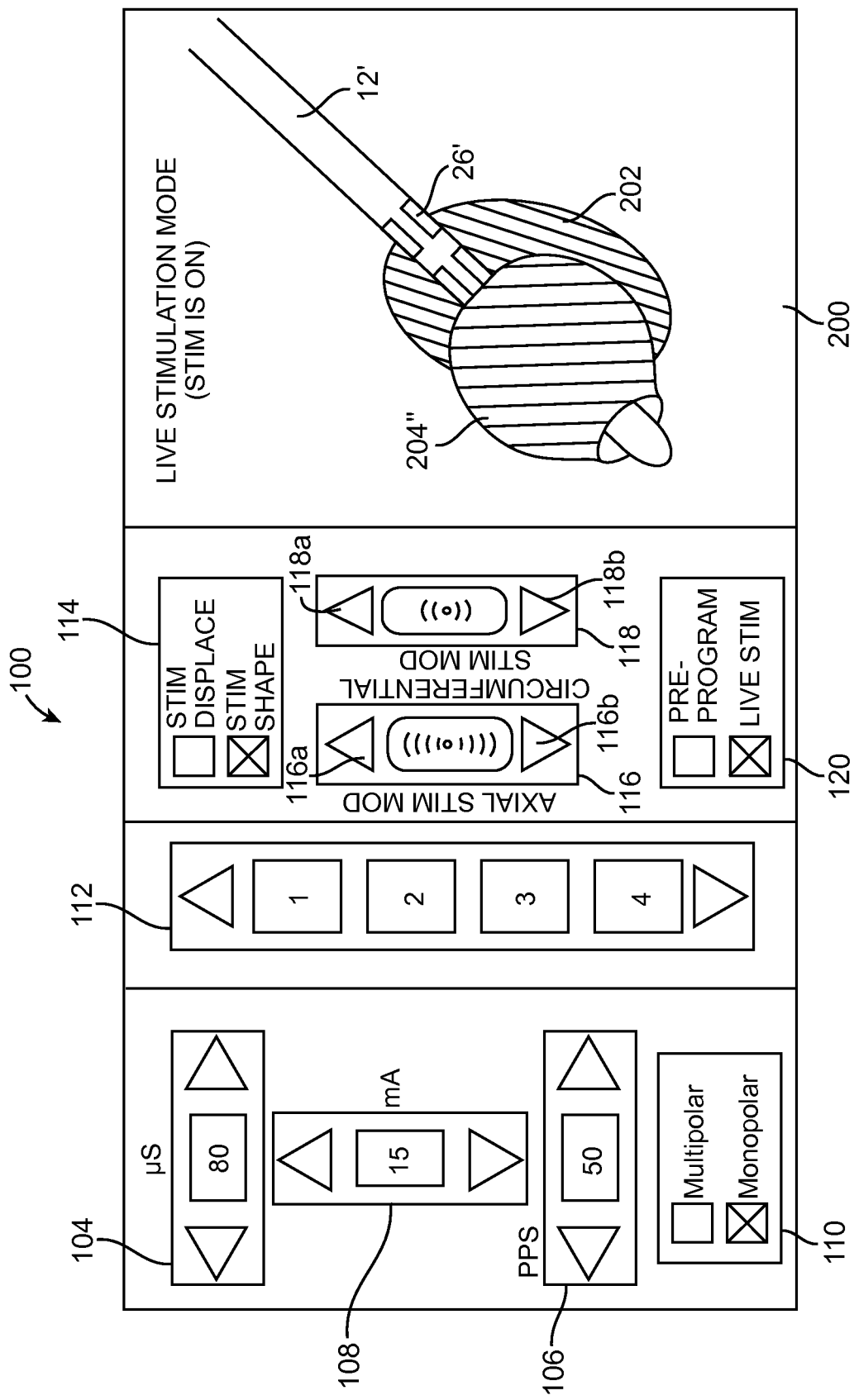

NEUROSTIMULATION SYSTEM FOR SELECTIVELY ESTIMATING VOLUME OF ACTIVATION AND PROVIDING THERAPY

RELATED APPLICATION DATA

The present application claims the benefit under 35 U.S.C. §119 to U.S. provisional patent application Ser. No. 61/427,441, filed Dec. 27, 2010. The foregoing application is hereby incorporated by reference into the present application in its entirety.

FIELD OF THE INVENTION

The present invention relates to tissue stimulation systems, and more particularly, to user interfaces and methods for controlling the distribution of electrical current on segmented neurostimulation leads.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Further, in recent investigations, Peripheral Nerve Stimulation (PNS) systems have demonstrated efficacy in the treatment of chronic pain syndromes and incontinence, and a number of additional applications are currently under investigation.

More pertinent to the present inventions described herein, Deep Brain Stimulation (DBS) has been applied therapeutically for well over a decade for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707, which are expressly incorporated herein by reference.

Each of these implantable neurostimulation systems typically includes one or more electrode carrying stimulation leads, which are implanted at the desired stimulation site, and a neurostimulator implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of movement disorders), while minimizing the volume of non-target tissue that is stimulated. A typical stimulation parameter set may include the electrodes that are acting as anodes or cathodes, as well as the amplitude, duration, and rate of the stimulation pulses.

Significantly, non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects.

For example, bilateral DBS of the subthalamic nucleus has been proven to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., *Reversing Cognitive-Motor Impairments in Parkinson's Disease Patients Using a Computational Modelling Approach to Deep Brain Stimulation Programming*, Brain 2010; pp. 1-16). In large part, this phenomenon is due to the small size of the subthalamic nucleus. Even with the electrodes are located predominately within the sensorimotor territory, the electrical field generated by DBS is non-discriminately applied to all neural elements surrounding the electrodes, thereby resulting in the spread of current to neural elements affecting cognition. As a result, diminished cognitive function during stimulation of the subthalamic nucleus may occur do to non-selective activation of non-motor pathways within or around the subthalamic nucleus.

The large number of electrodes available, combined with the ability to generate a variety of complex stimulation pulses, presents a huge selection of stimulation parameter sets to the clinician or patient. In the context of DBS, neurostimulation leads with a complex arrangement of electrodes that not only are distributed axially along the leads, but are also distributed circumferentially around the neurostimulation leads as segmented electrodes, can be used.

To facilitate such selection, the clinician generally programs the external control device, and if applicable the neurostimulator, through a computerized programming system. This programming system can be a self-contained hardware/software system, or can be defined predominantly by software running on a standard personal computer (PC). The PC or custom hardware may actively control the characteristics of the electrical stimulation generated by the neurostimulator to allow the optimum stimulation parameters to be determined based on patient feedback and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

As physicians and clinicians become more comfortable with implanting neurostimulation systems and time in the operating room decreases, post-implant programming sessions are becoming a larger portion of process. Furthermore, because the body tends to adapt to the specific stimulation parameters currently programmed into a neurostimulation system, or the full effects of stimulation are not manifest in a short period of time (i.e., not observed within a programming session), follow-up programming procedures are often needed.

For example, in the context of DBS, the brain is dynamic (e.g., due to disease progression, motor re-learning, or other changes), and a program (i.e., a set of stimulation parameters) that is useful for a period of time may not maintain its effectiveness and/or the expectations of the patient may increase. Further, physicians typically treat the patient with stimulation and medication, and proper amounts of each are required for optimal therapy. Thus, after the DBS system has been implanted and fitted, the patient may have to schedule another visit to the physician in order to adjust the stimulation parameters of the DBS system if the treatment provided by the implanted DBS system is no longer effective or otherwise is not therapeutically or operationally optimum due to, e.g., disease progression, motor re-learning, or other changes.

Regardless of the skill of the physician or clinician, neurostimulation programming sessions can be especially lengthy when programming complicated neurostimulation systems, such as DBS systems, where patient usually cannot feel the effects of stimulation, and the effects of the stimulation may be difficult to observe, are typically subjective, or otherwise may take a long time to become apparent. Typically, there is often a delay between selection of the stimulation parameters at the computerized programming system and the delivery of the stimulation to the patient in accordance with these parameters, mainly due to the forward and backward telemetry function between programming system and the neurostimulator. This makes it difficult to set the stimulation parameters appropriately or otherwise select stimulation parameters that result in optimal treatment for the patient and/or optimal use of the stimulation resources. Clinical estimates suggest that 18-36 hours per patient are necessary to program and assess DBS patients with current techniques (see Hunka K., et al., *Nursing Time to Program and Assess Deep Brain Stimulators in Movement Disorder Patients*, J. Neursci Nurs. 37: 204-10), which is an extremely large time commitment for both the physician/clinician and the patient.

There, thus, remains a need for a user interface that more efficiently allows the programming of neurostimulation systems.

SUMMARY OF THE INVENTION

In accordance with a first aspect of the present inventions, an external control device for use with a neurostimulator coupled to a plurality of electrodes capable of conveying electrical stimulation energy into tissue in which the electrodes are implanted is provided.

The external control device comprises output circuitry configured for transmitting sets of stimulation parameters to the neurostimulator, and a user interface including a display device and at least a first control element configured to be actuated to selectively place the external control device between a first mode and a second mode. In one embodiment, the user interface comprises at least another control element configured to be actuated to define the first one or more candidate stimulation parameter sets and the second one or more candidate stimulation parameter sets.

The external control device further comprises a processor that, when the external control device is in the first mode, is configured for simulating a volume of tissue activation for each of a first plurality of candidate stimulation parameter sets, while preventing the output circuitry from transmitting the first plurality of candidate stimulation parameter sets to the neurostimulator, and when the external control device is in the second mode, is configured for allowing the output circuitry to transmit a second plurality of candidate stimulation parameter sets to the neurostimulator.

In one embodiment, the user interface is configured for allowing the user to select one of the first plurality of candidate stimulation parameter sets, and the processor is configured for automatically using the user selected candidate stimulation parameter set as an initial one of the second plurality of candidate stimulation parameter sets during the second mode. In another embodiment, the processor is configured for scoring each simulated volume of tissue activation relative to a target tissue volume.

In an optional embodiment, the external control device further comprises memory configured for storing an anatomical representation (e.g., a brain model) having a target tissue volume (e.g., a subthalamic nucleus), which may be received by a user. In this case, the processor, when the external control device is in the first mode, may be configured for allowing the user interface to display each simulated volume of tissue activation relative to the target tissue volume on the monitor. The processor may also, when the external control device is in the second mode, be configured for simulating another volume of tissue activation for each of the second plurality of candidate stimulation parameter sets, and for allowing the user interface to display each other simulated volume of tissue activation relative to the target tissue volume. In this case, each volume of tissue activation displayed during the first mode can be represented with a first color, and each volume of tissue activation displayed during the second mode can be represented with a second color different from the first color.

In accordance with a second aspect of the present inventions, a neurostimulation system is provided. The neurostimulation system comprises a plurality of electrodes configured for being implanted within tissue, a neurostimulator coupled to the electrodes and configured for conveying electrical stimulation energy into the tissue via the electrodes, and an external control device having a first mode and a second mode.

The external control device is configured for, when in a first mode, simulating a volume of tissue activation for each of a first plurality of candidate stimulation parameter sets, while preventing the neurostimulator from conveying electrical stimulation energy, and when in an second mode, allowing the neurostimulator to convey electrical stimulation energy in accordance with the a second plurality of candidate stimulation parameter sets. In one embodiment, the external control device is configured for allowing a user to enter the first one or more candidate stimulation parameter sets and the second one or more candidate stimulation parameter sets. In another embodiment, the external control device is configured for allowing the user to select one of the first plurality of candidate stimulation parameter sets, and for automatically using the user selected candidate stimulation parameter set as an initial one of the second plurality of candidate stimulation parameter sets during the second mode. In still another embodiment, the external control device is configured for scoring each simulated volume of tissue activation relative to a target tissue volume.

In one preferred embodiment, the external control device is configured for storing an anatomical representation (e.g., a brain model) having a target tissue volume (e.g., a subthalamic nucleus), which may be received from the user, and when in the first mode, displaying each volume of tissue activation relative to the target tissue volume. The external control device, when in the second mode, may also configured for simulating another volume of tissue activation for each of the second plurality of candidate stimulation parameter sets, and displaying each other volume of tissue activation relative to the target tissue volume. In this case, the external control device may be configured for displaying an indicator that delineates the displaying of each volume of tissue activation from the displaying of each other volume of tissue activation. For example, the indicator may be a different color for the volume of tissue activation and the other volume of tissue activation.

In accordance with a third aspect of the present inventions, a method of programming a neurostimulator coupled to a plurality of electrodes that are implanted within the tissue of a patient is provided. The method comprises simulating a volume of tissue activation for each of a first plurality of candidate stimulation parameter sets without conveying electrical stimulation energy into the tissue, and selecting one of the first plurality of candidate stimulation parameter sets based on each simulated volume of tissue activation. The method further comprises conveying electrical stimulation energy into the tissue in accordance with a second plurality of candidate stimulation parameter sets, wherein the initial one of the second plurality of candidate stimulation parameter sets is the selected one of the first plurality of candidate stimulation parameter sets. The method further comprises selecting one of the second plurality of candidate stimulation parameter sets based on a therapeutic efficacy of the electrical stimulation energy conveyed into the tissue, and programming the neurostimulator with the selected one of the second plurality of candidate stimulation parameter sets.

One method further comprises scoring each simulated volume of tissue activation relative to a target tissue volume. In another method, each volume of tissue activation is displayed relative to a target tissue volume (e.g., a subthalamic nucleus). The method may further comprise simulating another volume of tissue activation for each of the second plurality of candidate stimulation parameter sets, and displaying each other volume of tissue activation relative to the target tissue volume. In this case, the method may further comprise displaying an indicator that delineates the displaying of each volume of tissue activation from the displaying of each other volume of tissue activation. For example, the indicator may be a different color for the volume of tissue activation and the other volume of tissue activation.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8B is a plan view of a live stimulation screen generated by the CP of FIG. 7.

DETAILED DESCRIPTION OF THE EMBODIMENTS

At the outset, it is noted that the present invention may be used with an implantable pulse generator (IPG), radio frequency (RF) transmitter, or similar neurostimulator, that may be used as a component of numerous different types of stimulation systems. The description that follows relates to a deep brain stimulation (DBS) system. However, it is to be understood that the while the invention lends itself well to applications in DBS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a spinal cord stimulator, peripheral nerve stimulator, microstimulator, or in any other neural stimulator configured to treat urinary incontinence, sleep apnea, shoulder sublaxation, headache, etc.

Figure 1:
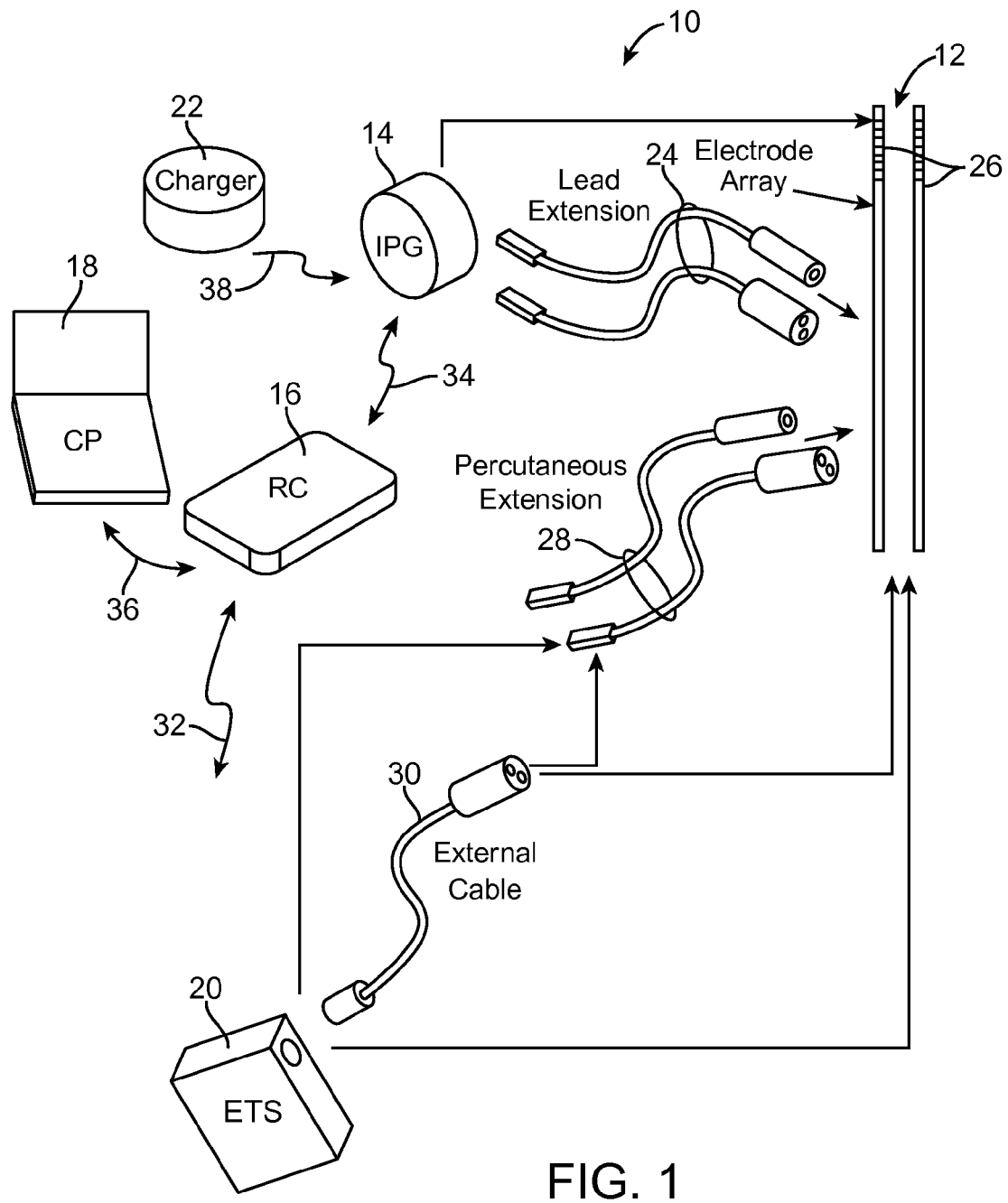
FIG. 1 is a plan view of a Deep Brain Stimulation (DBS) system constructed in accordance with one embodiment of the present inventions.

Turning first to FIG. 1, an exemplary DBS neurostimulation system 10 generally includes at least one implantable stimulation lead 12 (in this case, two), a neurostimulator in the form of an implantable pulse generator (IPG) 14, a remote controller RC 16, a clinician's programmer (CP) 18, an External Trial Stimulator (ETS) 20, and an external charger 22.

The IPG 14 is physically connected via one or more percutaneous lead extensions 24 to the neurostimulation leads 12, which carry a plurality of electrodes 26 arranged in an array. In the illustrated embodiment, the neurostimulation leads 12 are percutaneous leads, and to this end, the electrodes 26 may be arranged in-line along the neurostimulation leads 12. As will be described in further detail below, the IPG 14 includes pulse generation circuitry that delivers electrical stimulation energy in the form of a pulsed electrical waveform (i.e., a temporal plurality of electrical pulses) to the electrode array 26 in accordance with a set of stimulation parameters.

The ETS 20 may also be physically connected via the percutaneous lead extensions 28 and external cable 30 to the neurostimulation leads 12. The ETS 20, which has similar pulse generation circuitry as the IPG 14, also delivers electrical stimulation energy in the form of a pulse electrical waveform to the electrode array 26 accordance with a set of stimulation parameters. The major difference between the ETS 20 and the IPG 14 is that the ETS 20 is a non-implantable device that is used on a trial basis after the neurostimulation leads 12 have been implanted and prior to implantation of the IPG 14, to test the responsiveness of the stimulation that is to be provided. Thus, any functions described herein with respect to the IPG 14 can likewise be performed with respect to the ETS 20.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. As will be described in further detail below, the CP 18 provides clinician detailed stimulation parameters for programming the IPG 14 and ETS 20 in the operating room and in follow-up sessions.

The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

More significant to the present inventions, the CP 18 is capable of storing an anatomical representation, which in the case of DBS, will be a model of the patient's brain. The anatomical representation can be obtained from any available brain atlas, or from a patient specific brain atlas derived from, e.g., a magnetic resonant imager (MRI), computed tomography (CT), X-ray, fluoroscopy, ventriculography, ultrasound, or any other imaging modality or a merging of any or all of these modalities.

The anatomical representation has a target tissue volume, the stimulation of which is known or believed to provide the needed therapy to the patient. For example, if the DBS indication is Parkinson's disease, the target tissue volume may be the subthalamic nucleus (STN) or the globus pallidus (GPi). If the DBS indication is Essential Tremor, the target tissue volume may be the thalamus. If the DBS indication is depression, the target tissue volume may be one or more of the nucleus acumbens, ventral striatum, ventral capsule, anterior capsule, or the Brodmann's area 25. If the DBS indication is epilepsy, the target tissue volume may be preferably the anterior nucleus. If the DBS indication is a gait disorder, the target tissue volume may be the pedunculopontine nucleus (PPN). If the DBS indication is dementia, Alzheimer's disease or memory disorders, the target tissue volume may be anywhere in the Papez circuit. Notably, the targeted tissue volumes may not be strictly anatomical, but rather simply represent some volume of tissue that, when stimulated, provides therapy.

The target tissue volume may be pre-defined within the anatomical representation (e.g., an anatomical structure corresponding to the target tissue volume may naturally provide the boundaries that delineate it from the surrounding tissue, or a graphical marking corresponding to the target tissue volume may be incorporated into the anatomical representation prior to storing it within the CP 18) or the target tissue volume may be defined within the anatomical representation by the user (e.g., by graphically marking the anatomical representation as it is displayed on the CP 18.

The CP 18 is configured for being placed within either a "pre-programming" mode or a "live stimulation mode."

Advantageously, the pre-programming mode of the CP 18 allows the user to test candidate sets of stimulation parameters without actually conveying electrical stimulation energy to the patient, thereby obviating the need for the time-consuming telemetric functions between the CP 18 and the IPG 14 and patient feedback regarding the efficacy of the therapy.

In particular, when in the pre-programming mode, the CP 18 is configured for simulating a volume of tissue activation based on each candidate stimulation parameter set and displaying each simulated volume of tissue activation relative to the target tissue volume. The simulation of tissue volume activation can be performed in accordance with the modeling techniques referenced in Frankemolle AM, et al., *Reversing Cognitive-Motor Impairments in Parkinson's Disease Patients Using a Computational Modelling Approach to Deep Brain Stimulation Programming*, Brain 2010, March; 133 (Pt 3): 746-61, Epub 2010 Jan. 7. In the preferred embodiment, the CP 18 allows the user to enter the candidate stimulation parameter sets during the pre-programming mode in a conventional manner, although in other embodiments, the CP 18 may automatically step through pre-defined candidate stimulation parameter sets with minimal or no interaction by the user.

During the pre-programming mode, the CP 18 prevents the IPG 14 from conveying electrical stimulation energy, so that the volume of tissue activation simulation it performed totally "off-line" without having to telemetrically communicate with the IPG 14 and without having to rely on patient feedback. For the purposes of this specification, preventing a device or component from performing a function may comprise either affirmatively sending an instruction or control signal to that device or component to not perform the function or may comprise not sending an instruction or control signal otherwise required for the device or component to perform the function.

The efficacy of the candidate stimulation parameter set or sets may be determined by manually (i.e., looking at the display and manually analyzing the extent to which the resulting simulated volume of tissue matches the target tissue volume) or automatically by the CP 18 (e.g., using a scoring algorithm that determines the best candidate stimulation parameter set corresponding to the simulated volume of tissue activation that best covers the target tissue volume while minimizing the coverage of non-target tissue, which is described more fully in PCT Publication WO 2010/065888, and is expressly incorporated herein by reference). It can be appreciated from this that because the user does not have to wait for stimulation parameter sets to be communicated to the IPG 14 and patient feedback each time the candidate stimulation parameter set is changed, optimize or otherwise effective candidate stimulation parameter sets can be identified relatively quickly.

The live stimulation mode of the CP 18 allows the user to test candidate sets of stimulation parameters in a conventional manner; i.e., by actually conveying electrical energy to the patient in accordance with the different candidate stimulation parameter sets. However, the CP 18 may utilize what was learned during the pre-programming mode to more efficiently determine the candidate stimulation parameter set or sets that are optimum for the therapy. In particular, when in the live stimulation mode, the CP 18 is configured for allowing the IPG 14 to convey electrical stimulation energy in accordance with candidate stimulation parameter sets, so that they can be evaluated based on patient feedback in a conventional manner. For the purposes of this specification, allowing a device or component to perform a function may comprise either affirmatively sending an instruction or control signal to that device or component to perform the function or not sending an instruction or control signal otherwise required to prevent the device or component from performing the function. In the preferred embodiment, the CP 18 allows the user to enter the candidate stimulation parameter sets during the live stimulation mode in a conventional manner, although in other embodiments, the CP 18 may automatically step through pre-defined candidate stimulation parameter sets with minimal or no interaction with the user.

Advantageously, the CP 18 may select one of the candidate stimulation parameter sets tested when the CP 18 was in the pre-programming mode, and automatically use it as the initial candidate stimulation parameter set when the CP is in the live stimulation mode. Preferably, the selected candidate stimulation parameter is the optimum one obtained either by manual review by the user or via automatic scoring by the CP 18, so that an optimum or otherwise good starting point is provided at the beginning of the conventional programming process performed by the CP 18. It can be appreciated that by doing this, non-optimum or otherwise ineffective candidate stimulation parameter sets can be quickly eliminated when the CP 18 is operated in the pre-programming mode, whereas in the prior art, such non-optimum or ineffective candidate stimulation parameters are tediously eliminated during the conventional programming process.

In an optional embodiment, concurrent with allowing the IPG 14 to convey electrical stimulation energy, the CP 18, when in the live stimulation mode, is configured for simulating a volume of tissue activation based on each candidate stimulation parameter set and displaying each simulated volume of tissue activation relative to the target tissue volume. In this case, the CP 18 may provide an indication that delineates the pre-programming mode from the live stimulation mode, e.g., by using labels on the display and/or representing the simulated volume of tissue for the different modes with different colors.

Having generally described the neurostimulation system 10, the features of the neurostimulation system 10 will now be described in further detail.

Figure 2:
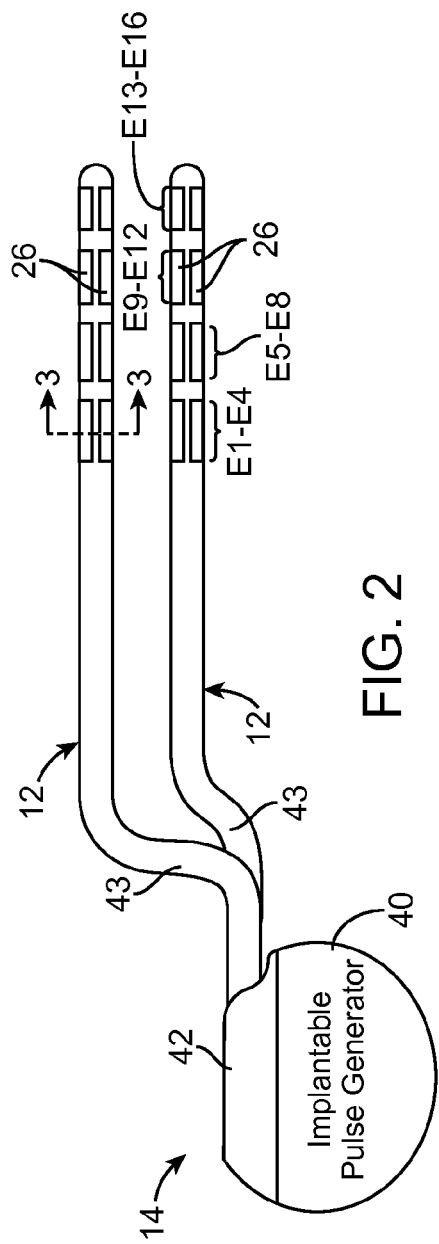
FIG. 2 is a profile view of an implantable pulse generator (IPG) and neurostimulation leads used in the DBS system of FIG. 1.

Referring to FIG. 2, the IPG 14 comprises an outer case 40 for housing the electronic and other components (described in further detail below), and a connector 42 to which the proximal end of the neurostimulation lead 12 mates in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

Figure 3:
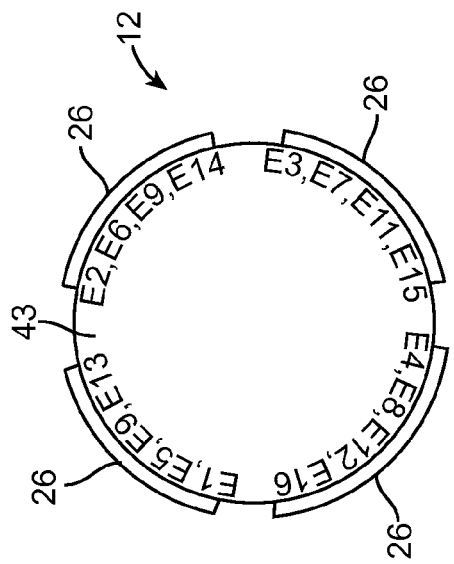
FIG. 3 is a cross-sectional view of a neurostimulation lead used in the DBS system of FIG. 1.

Each of the neurostimulation leads 12 comprises an elongated cylindrical lead body 43, and the electrodes 26 take the form of segmented electrodes that are circumferentially and axially disposed about the lead body 43. By way of non-limiting example, and with further reference to FIG. 3, each neurostimulation lead 12 may carry sixteen electrodes, arranged as four rings of electrodes (the first ring consisting of electrodes E1-E4; the second ring consisting of electrodes E5-E8; the third ring consisting of electrodes E9-E12; and the fourth ring consisting of E13-E16) or four axial columns of electrodes (the first column consisting of electrodes E1, E5, E9, and E13; the second column consisting of electrodes E2, E6, E10, and E14; the third column consisting of electrodes E3, E7, E11, and E15; and the fourth column consisting of electrodes E4, E8, E12, and E16). The actual number and shape of leads and electrodes will, of course, vary according to the intended application. Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

As will be described in further detail below, the IPG 14 includes a battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the stimulation on duration X and stimulation off duration Y).

Electrical stimulation will occur between two (or more) activated electrodes, one of which may be the IPG case. Simulation energy may be transmitted to the tissue in a monopolar or multipolar (e.g., bipolar, tripolar, etc.) fashion. Monopolar stimulation occurs when a selected one of the lead electrodes 26 is activated along with the case of the IPG 14, so that stimulation energy is transmitted between the selected electrode 26 and case. Bipolar stimulation occurs when two of the lead electrodes 26 are activated as anode and cathode, so that stimulation energy is transmitted between the selected electrodes 26. Tripolar stimulation occurs when three of the lead electrodes 26 are activated, two as anodes and the remaining one as a cathode, or two as cathodes and the remaining one as an anode.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other stimulators that may be used with the invention include stimulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

Figure 4:
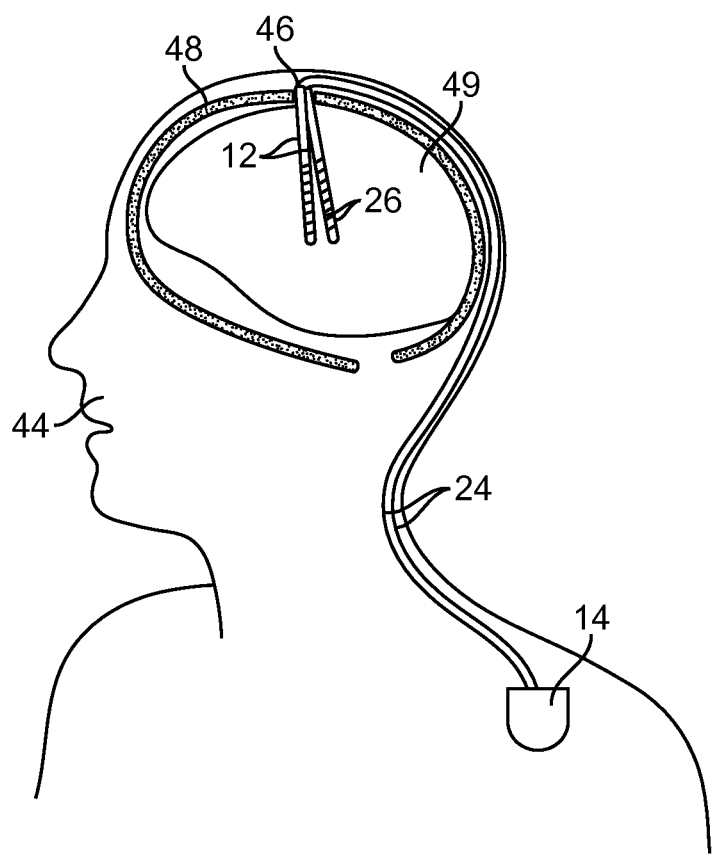
FIG. 4 is a cross-sectional view of a patient's head showing the implantation of stimulation leads and an IPG of the DBS system of FIG. 1.

As shown in FIG. 4, two percutaneous neurostimulation leads 12 may be introduced through a burr hole 46 (or alternatively, two respective burr holes) formed in the cranium 48 of a patient 44, and introduced into the parenchyma of the brain 49 of the patient 44 in a conventional manner, such that the electrodes 26 are adjacent a target tissue region, the stimulation of which will treat the dysfunction (e.g., the ventrolateral thalamus, internal segment of globus pallidus, substantia nigra pars reticulate, subthalamic nucleus, or external segment of globus pallidus). Thus, stimulation energy can be conveyed from the electrodes 26 to the target tissue region to change the status of the dysfunction. Due to the lack of space near the location where the neurostimulation leads 12 exit the burr hole 46, the IPG 14 is generally implanted in a surgically-made pocket either in the chest, or in the abdomen. The IPG 14 may, of course, also be implanted in other locations of the patient's body. The lead extension(s) 24 facilitates locating the IPG 14 away from the exit point of the neurostimulation leads 12.

Figure 5:
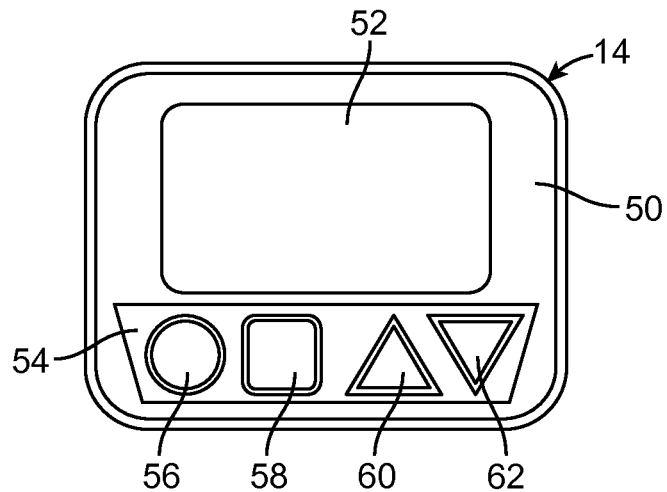
FIG. 5 is front view of a remote control (RC) used in the DBS system of FIG. 1.

Referring now to FIG. 5, one exemplary embodiment of an RC 16 will now be described. As previously discussed, the RC 16 is capable of communicating with the IPG 14, CP 18, or ETS 20. The RC 16 comprises a casing 50, which houses internal componentry (including a printed circuit board (PCB)), and a lighted display device 52 and button pad 54 carried by the exterior of the casing 50. In the illustrated embodiment, the display device 52 is a lighted flat panel display device, and the button pad 54 comprises a membrane switch with metal domes positioned over a flex circuit, and a keypad connector connected directly to a PCB. In an optional embodiment, the display device 52 has touchscreen capabilities. The button pad 54 includes a multitude of buttons 56, 58, 60, and 62, which allow the IPG 14 to be turned ON and OFF, provide for the adjustment or setting of stimulation parameters within the IPG 14, and provide for selection between screens.

In the illustrated embodiment, the button 56 serves as an ON/OFF button that can be actuated to turn the IPG 14 ON and OFF. The button 58 serves as a select button that allows the RC 16 to switch between screen displays and/or parameters. The buttons 60 and 62 serve as up/down buttons that can actuated to increment or decrement any of stimulation parameters of the pulse generated by the IPG 14, including pulse amplitude, pulse width, and pulse rate. For example, the selection button 58 can be actuated to place the RC 16 in an "Pulse Amplitude Adjustment Mode," during which the pulse amplitude can be adjusted via the up/down buttons 60, 62, a "Pulse Width Adjustment Mode," during which the pulse width can be adjusted via the up/down buttons 60, 62, and a "Pulse Rate Adjustment Mode," during which the pulse rate can be adjusted via the up/down buttons 60, 62. Alternatively, dedicated up/down buttons can be provided for each stimulation parameter. Rather than using up/down buttons, any other type of actuator, such as a dial, slider bar, or keypad, can be used to increment or decrement the stimulation parameters. Further details of the functionality and internal componentry of the RC 16 are disclosed in U.S. Pat. No. 6,895,280, which has previously been incorporated herein by reference.

Figure 6:
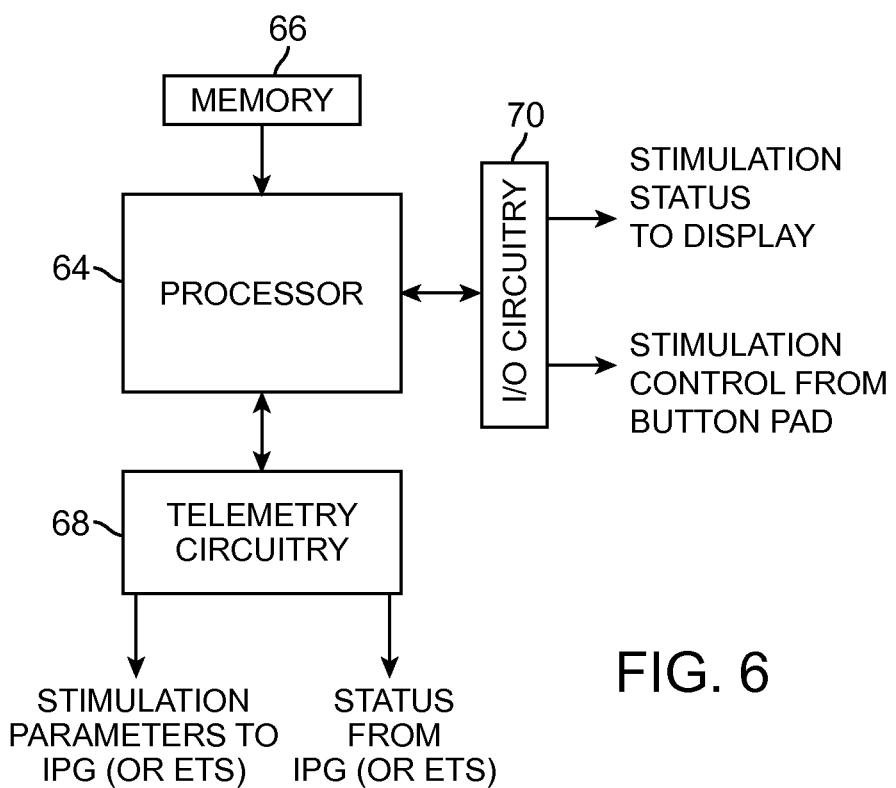
FIG. 6 is a block diagram of the internal components of the RC of FIG. 5.

Referring to FIG. 6, the internal components of an exemplary RC 16 will now be described. The RC 16 generally includes a processor 64 (e.g., a microcontroller), memory 66 that stores an operating program for execution by the processor 64, as well as stimulation parameter sets in a look-up table (described below), input/output circuitry, and in particular, telemetry circuitry 68 for outputting stimulation parameters to the IPG 14 and receiving status information from the IPG 14, and input/output circuitry 70 for receiving stimulation control signals from the button pad 54 and transmitting status information to the display device 52 (shown in FIG. 5). As well as controlling other functions of the RC 16, which will not be described herein for purposes of brevity, the processor 64 generates new stimulation parameter sets in response to the user operation of the button pad 54. These new stimulation parameter sets would then be transmitted to the IPG 14 via the telemetry circuitry 68. Further details of the functionality and internal componentry of the RC 16 are disclosed in U.S. Pat. No. 6,895,280, which has previously been incorporated herein by reference.

As briefly discussed above, the CP 18 greatly simplifies the programming of multiple electrode combinations, allowing the physician or clinician to readily determine the desired stimulation parameters to be programmed into the IPG 14, as well as the RC 16. Thus, modification of the stimulation parameters in the programmable memory of the IPG 14 after implantation is performed by a clinician using the CP 18, which can directly communicate with the IPG 14 or indirectly communicate with the IPG 14 via the RC 16. That is, the CP 18 can be used by the physician or clinician to modify operating parameters of the electrode array 26 in the brain.

The overall appearance of the CP 18 is that of a laptop personal computer (PC), and in fact, may be implanted using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum stimulation parameters to be determined based on patient response and feedback and for subsequently programming the IPG 14 with the optimum stimulation parameters.

Figure 7:
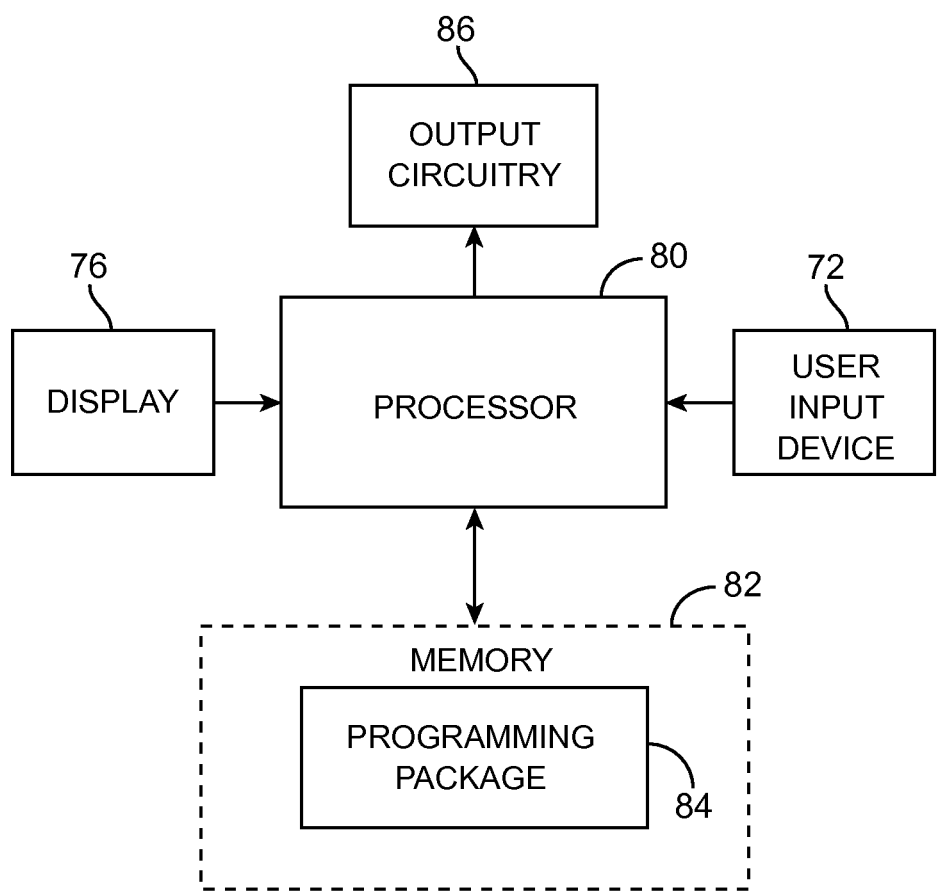
FIG. 7 is a block diagram of the internal components of a clinician's programmer (CP) used in the DBS system of FIG. 1.

Referring to FIG. 7, to allow the user to perform these functions, the CP 18 includes a standard user input device 72 (e.g., a keyboard, mouse, joystick, etc.) to allow a clinician to input information and control the process and a display device 76 housed in a case. In the illustrated embodiment, the monitor 76 is a conventional screen. Alternatively, instead of being conventional, the monitor 76 may be a digitizer screen, such as touchscreen (not shown), and may be used in conjunction with an active or passive digitizer stylus/finger touch.

The CP 18 generally includes a processor 80 (e.g., a central processor unit (CPU)) and memory 82 that stores a stimulation programming package 84, which can be executed by the processor 80 to allow the user to program the IPG 14, and RC 16. The memory 82 also stores the anatomical representation, and in this case, a representation of the brain, as described above. The CP 18 further includes output circuitry 86 (e.g., via the telemetry circuitry of the RC 16) for downloading stimulation parameters to the IPG 14 and RC 16 and for uploading stimulation parameters already stored in the memory 66 of the RC 16, via the telemetry circuitry 68 of the RC 16.

Execution of the programming package 84 by the processor 80 provides a multitude of display devices (not shown) that can be navigated through via the user input device 72. These display devices allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical stimulation energy output by the leads 12, and select and program the IPG 14 with stimulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Stimulation Energy Among Multiple Neurostimulation Electrodes," which are expressly incorporated herein by reference.

Most pertinent to the present inventions, execution of the programming package 84 provides a user interface that allows the CP 18 to be operated in the previously described pre-programming mode and programming mode, during which a simulated or actual electrical stimulation field conveyed by selected ones of the electrodes 26 can be modified, e.g., by axially, circumferentially, and/or radially displacing the locus of the stimulation field circumferentially relative to a single neurostimulation lead 12 or both neurostimulation leads 12, and axially and/or circumferentially expanding or contracting the electrical stimulation field about its locus. Further details discussing various methods that can be used to modify an electrical stimulation field are described in U.S. Provisional Patent Application Ser. No. 61/374,465, entitled "User Interface for Segmented Neurostimulation Leads.

Figure 8A:
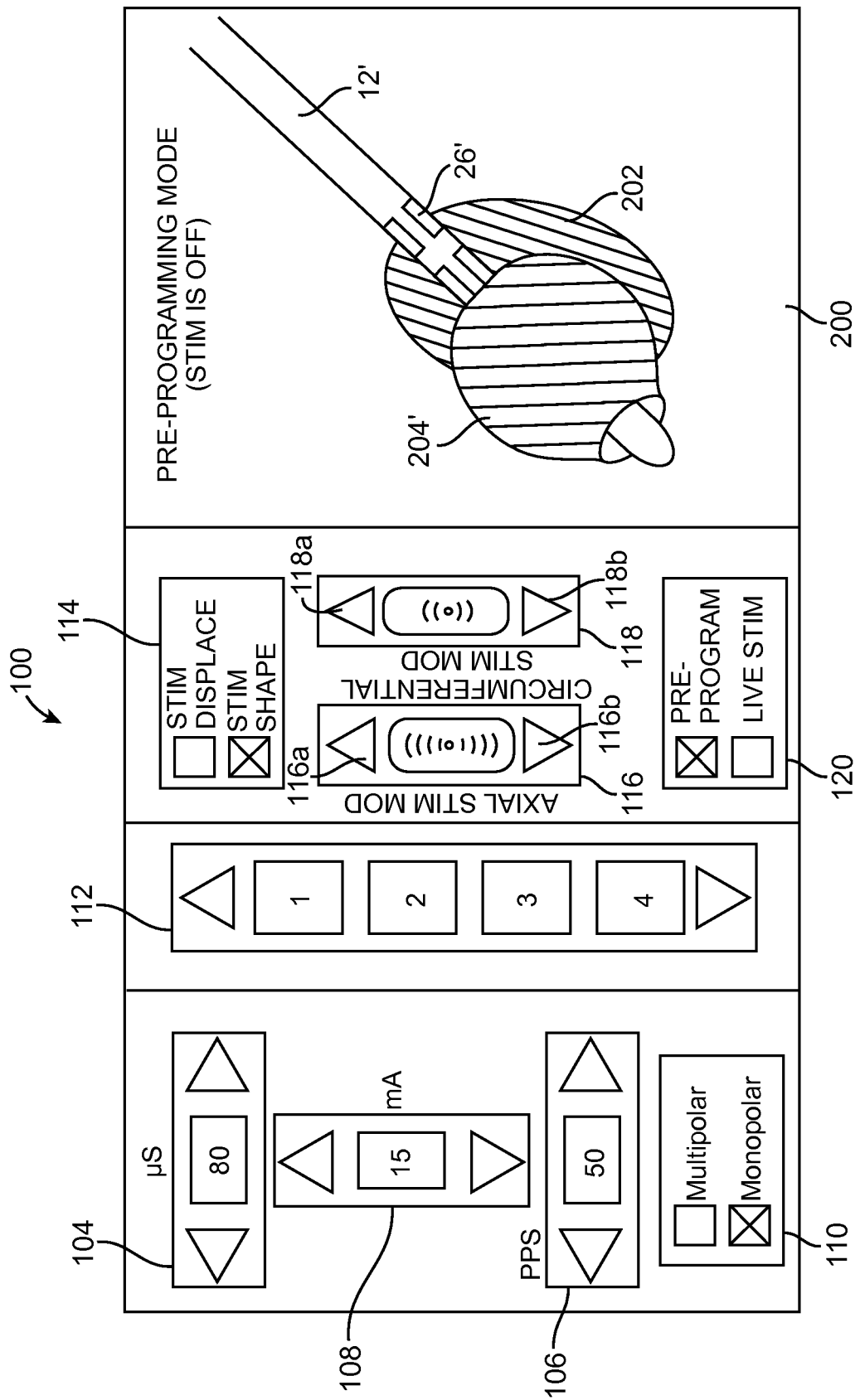
FIG. 8A is a plan view of a pre-programming screen generated by the CP of FIG. 7.

Referring to FIGS. 8a and 8b, a pre-programming screen 100' and a live stimulation screen 100" (collectively, the programming screens 100) allowing a user to perform stimulation parameter testing can be generated by the CP 18. In the illustrated embodiment, various control elements displayed on the programming screen 100 are implemented as graphical icons that can be clicked with a mouse or touched with a finger in the case of a touchscreen. Alternatively, any of the control elements described herein may be implemented as mechanical buttons, keys, sliders, etc. that can be pressed or otherwise moved to actuate the control elements.

The programming screen 100 includes various stimulation parameter controls that can be operated by the user to manually adjust or otherwise define stimulation parameters. Such stimulation parameter adjustment can be performed in any one or more of a variety of manners, e.g., using look-up tables, formulas, or algorithms, as is known in the prior art.

In particular, the programming screen 100 includes a pulse width adjustment control 104 (expressed in microseconds (ps)), a pulse rate adjustment control 106 (expressed in pulses per second (pps), and a pulse amplitude adjustment control 108 (expressed in milliamperes (mA)). Each control includes a first arrow that can be clicked to decrease the value of the respective stimulation parameter and a second arrow that can be clicked to increase the value of the respective stimulation parameter. The programming screen 100 also includes multipolar/monopolar stimulation selection control 110, which includes check boxes that can be alternately clicked by the user to provide multipolar or monopolar stimulation. In an optional embodiment, the case 40 of the IPG 14 may be treated as one of the lead electrodes 26, such that both the case electrode 40 and at least one of the lead electrodes 26 can be used to convey anodic electrical current at the same time.

The programming screen 100 also includes an electrode combination control 112 having arrows that can be clicked by the user to select one of three different electrode combinations 1-4. Each of the electrode combinations 1-4 can be created using a variety of control elements.

The programming screen 100 also includes a mode selection control element 114 and two sets of electrical stimulation field modification control elements—a set of axial modification control elements 116 and a set of circumferential modification control elements 118. When the mode selection control element 114 is actuated, the processor 80 is configured for selectively placing the field modification control elements in either an electrical stimulation field displacement mode, during which the processor 80 generates stimulation parameter sets designed to axially and/or circumferentially displace the locus of the electrical stimulation field relative to the axis of the lead(s) 12 upon actuation of one of the arrow control elements 116a, 116b or one of the arrow control elements 118a, 118b, or in an electrical field stimulation field shaping mode, during which the processor 80 generates stimulation parameter sets designed to axially or circumferentially expand/contract electrical stimulation field relative to the axis of the lead(s) 12 upon actuation of one of the arrow control elements 116a, 116b or one of the arrow control elements 118a, 118b.

In the illustrated embodiment, the mode selection control element 114 includes check boxes that can be alternately clicked by the user to selectively place the field modification control elements between the electrical stimulation field displacement mode and the electrical stimulation field shaping mode. Alternatively, the mode selection control element 114 takes the form of a button that can be repeatedly clicked to toggle the field modification control elements 116, 118 between the modes. Optionally, a set of radial modification control elements (not shown) can be provided. Further details discussing the illustrated control elements of programming screen 100, as well as other control elements for varying the electrical stimulation field, are described in U.S. Provisional Patent Application Ser. No. 61/374,879, which was previously incorporated herein by reference.

Significantly, the programming screen 100 includes a programming mode control element 120 that allows a user to selectively place the CP 18 in either the pre-programming mode or the live stimulation mode. In the illustrated embodiment, actuation of the programming mode control element 120 toggles the CP 18 between the pre-programming mode and the live stimulation mode. In alternative embodiments, separate control elements (not shown) can be respectively provided for the pre-programming mode and the live stimulation mode.

The processor 80 is configured for instructing the display device 76 to display three-dimensional graphical renderings of the lead 12' and electrodes 26' relative to the anatomical representation 200, which in this case, is a model of a brain having a target tissue volume 202, and in particular, the STN.

When the CP 18 is in the pre-programming mode (FIG. 8a), the processor 80 is configured for simulating a volume of tissue activation 204' for each of the candidate stimulation parameter sets generated in response to actuation of any of the field modification control elements 116, 118, and instructing the display device 76 to display, on the pre-programming screen 100', the simulated volume of tissue activation 204' relative to the anatomical representation 200, while preventing the output circuitry 86 from transmitting the candidate stimulation parameter sets to the IPG 14. In the preferred embodiment, the volume of tissue activation 204' is superimposed over the anatomical representation 200. In the illustrated embodiment, although the graphical lead 12, anatomical representation 200, and volume of tissue activation 204' are displayed in an oblique view, they can be alternatively displayed in any one or more of traditional planes of section (e.g., axial, coronal, and sagittal).

When the CP 18 is in the live stimulation mode (FIG. 8*b*), the processor 80 is configured for instructing the output circuitry 86 to transmit candidate stimulation parameter sets generated in response to actuation of any of the field modification control elements 116, 118 to the IPG 14. In an optional embodiment, concurrently with the transmission of the candidate stimulation parameter sets to the IPG 14, the processor 80 is configured for simulating a volume of tissue activation 204'' for each of the candidate stimulation parameter sets generated in response to actuation of any of the field modification control elements 116, 118, and instructing the display device 76 to display, on the live stimulation screen 100'', the simulated volume of tissue activation 204'' relative to the anatomical representation 200, in the manner described above with respect to the pre-programming mode.

In the illustrated embodiment, an indicator is used to distinguish when the CP 18 is in the pre-programming mode (when no stimulation energy is conveyed from the IPG 14) and when the CP 18 is in the live stimulation mode (when stimulation is conveyed from the IPG 14). In the illustrated embodiment, the pre-programming screen 100' (FIG. 8*a*) has a textual indication "pre-programming mode," and the live stimulation screen 100'' (FIG. 8*b*) has a textual indication "live stimulation mode." The colors of the simulated volumes of tissue 204 displayed in the respective programming screens 100' and 100'' may also be different. For example, the color of the simulated volume of tissue 204' displayed in the pre-programming screen 100' may be a grey color and the color of the simulated volume of tissue 204'' displayed in the live stimulation screen 100'' may be a green color.

The CP 18 allows the user to select one of the candidate stimulation parameter sets tested during the pre-programming mode to be used during operation in the live stimulation mode. In the illustrated embodiment, when the programming mode control element 120 is actuated to transition the CP 18 from the pre-programming mode to the live stimulation mode, the processor 80 uses the last candidate parameter set tested in the pre-programming mode as the initial candidate stimulation parameter set tested during the live stimulation mode. In an alternative embodiment, the CP 18 allows the user to select any candidate stimulation parameter tested during the pre-programming mode to be used as the initial candidate stimulation parameter set tested during the live stimulation mode. For each candidate stimulation parameter set tested during the pre-programming mode, the processor 80 may score the simulated volume of tissue activation 204' relative to the target tissue volume 202, and either the user may select one of the candidate stimulation parameter sets based on the scores (e.g., the candidate stimulation parameter set corresponding to the highest score) for use as the initial candidate stimulation parameter set during the live stimulation mode, or the processor 80 may automatically select the candidate stimulation parameter set based on the scores.

Figure 9:
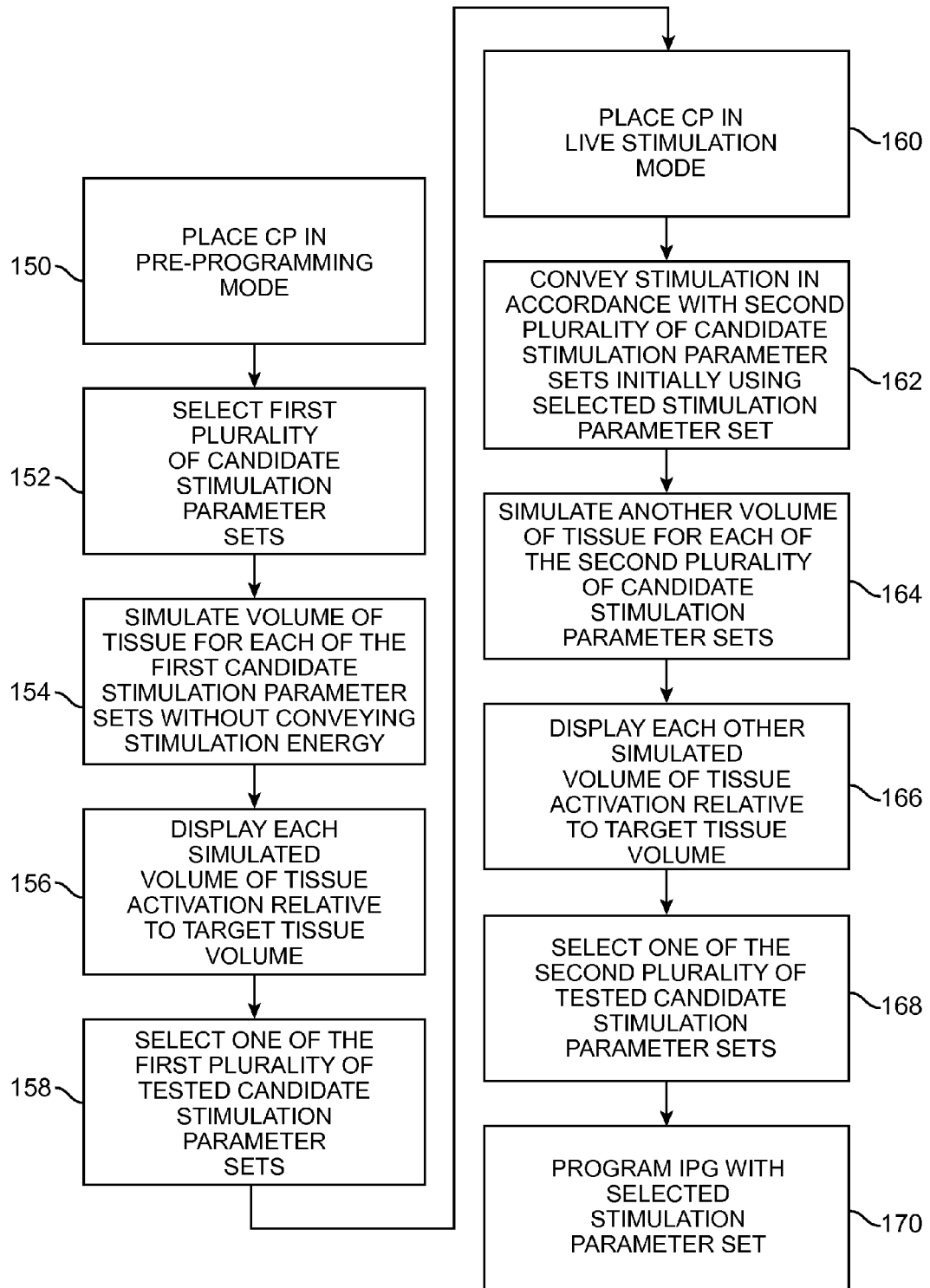
FIG. 9 is a flow diagram illustrating one method of programming the IPG of FIG. 2.

Having described the arrangement and function of the components within the neurostimulation system 10, one method of programming the IPG 14 will now be described with respect to FIG. 9.

First, if the CP 18 is not already in the pre-programming mode, the user actuates the mode selection control element 120 to place the CP 18 in the pre-programming mode (step 150). Then, the user serially selects a plurality of candidate stimulation parameter sets to be tested by repeatedly actuating the electrical stimulation field modification elements 116, 118 (step 152). The CP 18 simulates a volume of tissue activation for each of these candidate stimulation parameter sets without conveying electrical stimulation energy from the IPG 14 (step 154), and displays each simulated volume of tissue activation relative to the target tissue volume (in this case, the STN) (step 156). Then, one of the tested candidate stimulation parameter sets is selected based on each simulated volume of tissue activation (step 158). For example, the user may look at each simulated volume of tissue activation displayed relative to the target tissue volume, and determine based on that, which one of the tested candidate stimulation parameter sets is the most effective. Or the CP 18 may score each simulated volume of tissue relative to the target tissue volume, and select the tested candidate stimulation parameter set corresponding to the highest score.

Next, the user actuates the mode selection control element 120 to place the CP 18 in the live stimulation mode (step 160). Using the selected candidate stimulation parameter set as an initial candidate stimulation parameter set, electrical stimulation energy is conveyed into the tissue serially in accordance with a respective second plurality of candidate stimulation parameter sets (step 162). An optional method may further comprise simulating another volume of tissue activation for each of the second plurality of candidate stimulation parameter sets (step 164), and displaying each other volume of tissue activation relative to the target tissue volume (step 166). In a conventional manner, one of the second plurality of candidate stimulation parameter sets can be selected based on a therapeutic efficacy of the electrical stimulation energy conveyed into the tissue (e.g., based on patient feedback) (step 168). The selected candidate stimulation parameter set can then be programmed into non-volatile memory in the IPG 14 for subsequent selection by the user (step 170). If need be, the process can then be repeated to program the IPG 14 with another candidate stimulation parameter set.

Although the foregoing techniques have been described as being implemented in the CP 16, it should be noted that this technique may be alternatively or additionally implemented in the RC 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An external control device for use with a neurostimulator coupled to a plurality of electrodes capable of conveying electrical stimulation energy into tissue in which the electrodes are implanted, comprising:

output circuitry configured for communicating with the neurostimulator;

a user interface including a display device and at least a first control element configured to be actuated to selectively place the external control device between a first mode and a second mode, and at least a second control element configured to be actuated to define a plurality of different candidate electrode combinations; and a processor, when the external control device is in the first mode, configured for simulating a volume of tissue activation based on each of a first one or more candidate electrode combinations, while preventing the output circuitry from transmitting the first one or more of candidate electrode combinations to the neurostimulator in response to the definition of each of the first one or more electrode combinations, and when the external control device is in the second mode, configured for allowing the output circuitry to transmit a second one or more of candidate electrode combinations to the neurostimulator.

2. The external control device of claim 1, wherein the first one or more candidate electrode combinations comprises a plurality of candidate electrode combinations, wherein the user interface is configured for allowing the user to select one of the plurality of candidate electrode combinations, and wherein the processor is configured for automatically using the user selected candidate electrode combination as an initial one of the second one or more candidate electrode combinations during the second mode.

3. The external control device of claim 1, wherein the processor is configured for scoring each simulated volume of tissue activation relative to a target tissue volume.

4. The external control device of claim 1, further comprising memory configured for storing an anatomical representation having a target tissue volume, wherein the processor, when the external control device is in the first mode, is configured for allowing the user interface to display each simulated volume of tissue activation relative to the target tissue volume on the monitor.

5. The external control device of claim 4, wherein the processor, when the external control device is in the second mode, is configured for simulating another volume of tissue activation for each of the second one or more candidate electrode combinations, and for allowing the user interface to display each other simulated volume of tissue activation relative to the target tissue volume.

6. The external control device of claim 5, wherein each volume of tissue activation is represented with a first color, and each other volume of tissue activation is represented with a second color different from the first color.

7. The external control device of claim 4, wherein the user interface is configured for receiving the anatomical representation from a user.

8. The external control device of claim 4, wherein the anatomical representation is a brain model.

9. The external control device of claim 8, wherein the target tissue volume is a subthalamic nucleus.

10. The external control device of claim 1, further comprising a housing containing the output circuitry, user interface, and processor.

11. The external control device of claim 1, wherein the plurality of different candidate electrode combinations comprises a plurality of different candidate fractionalized electrode combinations.

12. A neurostimulation system, comprising:
a plurality of electrodes configured for being implanted within tissue;
a neurostimulator coupled to the electrodes and configured for conveying electrical stimulation energy into the tissue via the electrodes; and
an external control device configured for allowing a user to enter a first one or more candidate electrode combinations and a second one or more candidate electrode combinations, the external control device having a first mode and a second mode, the external control device configured for, when in a first mode, simulating a volume of tissue activation based on each of the first one or more candidate electrode combinations, while preventing the neurostimulator from conveying electrical stimulation energy in response to the user entry of each of the first one or more candidate electrode combinations, and when in an second mode, allowing the neurostimulator to convey electrical stimulation energy in accordance with the second one or more candidate electrode combinations.

13. The neurostimulation system of claim 12, wherein the first one or more candidate electrode combinations comprises a plurality of candidate electrode combinations, wherein the external control device is configured for allowing the user to select one of the plurality of candidate electrode combinations, and for automatically using the user selected candidate electrode combination set as an initial one of the second one or more candidate electrode combinations during the second mode.

14. The neurostimulation system of claim 12, wherein the external control device is configured for scoring each simulated volume of tissue activation relative to a target tissue volume.

15. The neurostimulation system of claim 12, wherein the external control device is configured for storing an anatomical representation having a target tissue volume, and when in the first mode, displaying each volume of tissue activation relative to the target tissue volume.

16. The neurostimulation system of claim 15, wherein the external control device, when in the second mode, is configured for simulating another volume of tissue activation for each of the second one or more candidate electrode combinations, and displaying each other volume of tissue activation relative to the target tissue volume.

17. The neurostimulation system of claim 16, wherein the external control device is configured for displaying an indicator that delineates the displaying of each volume of tissue activation from the displaying of each other volume of tissue activation.

18. The neurostimulation system of claim 17, wherein the indicator is a different color for the volume of tissue activation and the other volume of tissue activation.

19. The neurostimulation system of claim 15, wherein the external control device is configured for receiving the anatomical representation from a user.

20. The neurostimulation system of claim 15, wherein the anatomical representation is a brain model.

21. The neurostimulation system of claim 20, wherein the target tissue volume is a subthalamic nucleus.

22. The neurostimulation system of claim 12, wherein the first one or more candidate electrode combinations and the second one or more candidate electrode combinations are fractionalized electrode combinations.

23. A method of programming a neurostimulator coupled to a plurality of electrodes that are implanted within the tissue of a patient, comprising:
simulating a volume of tissue activation based on each of a first plurality of candidate electrode combinations without conveying electrical stimulation energy into the tissue;
selecting one of the first plurality of candidate electrode combinations based on each simulated volume of tissue activation;
conveying electrical stimulation energy into the tissue in accordance with a second one or more candidate electrode combinations, wherein the initial one of the second one or more candidate electrode combinations is the selected one of the first plurality of candidate electrode combinations;

selecting one of the second one or more candidate electrode combinations based on a therapeutic efficacy of the electrical stimulation energy conveyed into the tissue; and programming the neurostimulator with the selected one of the second one or more candidate electrode combinations.

24. The method of claim 23, further comprising scoring each simulated volume of tissue activation relative to a target tissue volume.

25. The method of claim 23, wherein each volume of tissue activation is displayed relative to a target tissue volume.

26. The method of claim 25, further comprising simulating another volume of tissue activation for each of the second one or more candidate electrode combinations, and displaying each other volume of tissue activation relative to the target tissue volume.

27. The method of claim 26, further comprising displaying an indicator that delineates the displaying of each volume of tissue activation from the displaying of each other volume of tissue activation.

28. The method of claim 27, wherein the indicator is a different color for the volume of tissue activation and the other volume of tissue activation.

29. The method of claim 25, wherein the target tissue volume is a subthalamic nucleus.

30. The method of claim 23, wherein the first plurality of candidate electrode combinations and the second one or more electrode combinations are fractionalized electrode combinations.

* * * * *